(12) United States Patent
Althaus et al.

(10) Patent No.: US 9,079,850 B2
(45) Date of Patent: Jul. 14, 2015

(54) COSMETIC COMPOSITIONS CONTAINING ESTERS OF 2-ETHYLBUTANOL

(75) Inventors: Stefanie Althaus, Köln (DE); Markus Dierker, Düsseldorf (DE); Daniela Prinz, Dormagen (DE); Catherine Weichold, Aachen (DE)

(73) Assignee: Cognis IP Management GmbH, Duesseldorf (DE)

( * ) Notice: Subject to any disclaimer, the term of this patent is extended or adjusted under 35 U.S.C. 154(b) by 1055 days.

(21) Appl. No.: 12/377,947

(22) PCT Filed: Aug. 9, 2007

(86) PCT No.: PCT/EP2007/007036
§ 371 (c)(1),
(2), (4) Date: Feb. 18, 2009

(87) PCT Pub. No.: WO2008/019793
PCT Pub. Date: Feb. 21, 2005

(65) Prior Publication Data
US 2010/0292328 A1    Nov. 18, 2010

(30) Foreign Application Priority Data
Aug. 18, 2006  (EP) .................................. 06017218

(51) Int. Cl.
- *C07C 69/24* (2006.01)
- *A61K 8/37* (2006.01)
- *A61K 8/39* (2006.01)
- *A61K 8/60* (2006.01)
- *A61K 8/86* (2006.01)
- *A61Q 19/10* (2006.01)
- *A61Q 5/12* (2006.01)

(52) U.S. Cl.
CPC . *C07C 69/24* (2013.01); *A61K 8/37* (2013.01); *A61K 8/39* (2013.01); *A61K 8/604* (2013.01); *A61K 8/86* (2013.01); *A61Q 19/10* (2013.01); *A61Q 5/12* (2013.01)

(58) Field of Classification Search
CPC .................................. C07C 69/24; A61K 8/37
USPC ......................................................... 424/401
See application file for complete search history.

(56) References Cited

U.S. PATENT DOCUMENTS

| | | | |
|---|---|---|---|
| 2,576,899 A | 11/1951 | Albrecht | |
| 3,031,493 A | 4/1962 | Enk et al. | |
| 3,099,603 A | 7/1963 | Banker et al. | |
| 4,464,290 A * | 8/1984 | Ohta et al. | 512/5 |
| 4,652,401 A * | 3/1987 | Schaper et al. | 512/21 |
| 5,686,087 A | 11/1997 | Ansmann et al. | |
| 5,762,947 A * | 6/1998 | Guerrero et al. | 424/401 |
| 6,156,387 A | 12/2000 | Werres et al. | |
| 6,346,258 B1 * | 2/2002 | Kramer | 424/401 |
| 7,208,545 B1 | 4/2007 | Brunner et al. | |
| 2005/0019353 A1 | 1/2005 | Prinz et al. | |
| 2005/0089497 A1 | 4/2005 | Prinz et al. | |

FOREIGN PATENT DOCUMENTS

| | | |
|---|---|---|
| DE | 19616733 A1 | 11/1997 |
| DE | 19927978 A1 | 12/2000 |
| DE | 10160681 A1 | 6/2003 |
| DE | 10160682 A1 | 6/2003 |
| EP | 0098791 A1 | 1/1984 |
| EP | 0375827 A2 | 7/1990 |
| EP | 0766661 B1 | 4/1997 |
| GB | 896436 | 5/1962 |
| GB | 1092401 | 11/1967 |
| GB | 1108067 | 4/1968 |
| JP | 58164504 | 9/1983 |
| JP | H09-506359 | 6/1997 |
| JP | 2006-176754 | 7/2006 |
| WO | 8503517 A1 | 8/1985 |
| WO | 8703780 A1 | 7/1987 |
| WO | 95/34528 A1 | 12/1995 |
| WO | 2006057090 A1 | 1/2006 |

OTHER PUBLICATIONS

"Alphatic Esters" Properties and Lubricant Applications XP-002417985 G. Cohen et al., Aug. 1953, Industrial and Engineering Chemistry pp. 1766-1775.

"Synthetic Lubricant Fluids from Branched-Chain Diesters" Physical and Chemical Properties of Pure Diesters XP-002417984; E.M. Bried et al. Apr. 1947, Industrial and Engineering Chemistry pp. 484-491.

"Die Butyrate und ihre Verwendung in der Riechstoff-, Aromen- und Parfumerie- sowie Seifen-Industrie" XP009094651; W. L. Hoffman, Sep. 1959, Riechstoffe und Aromen, No. 9 9. Jahrgang pp. 273-277.

"Encyclopedia of Chemical Technology" Diuretics to Emulsions, Kirk-Othmer 1979, Third Edition, vol. 8.

"Huaxue Tongboa" Y. Wu et al. 1985, (5), 19-24.

Gassenmeier, Thomas et al., "Sensory Assessment of Lipids in Leave-On and Rinse-Off Products", *Cosmetic Lipids and the Skin Barrier*, 20 pgs.

* cited by examiner

*Primary Examiner* — Gina Justice
(74) *Attorney, Agent, or Firm* — Servilla Whitney LLC

(57) ABSTRACT

The invention relates to the use of esters of 2-ethylbutanol with $C_{4-36}$ dicarboxylic acids or $C_{4-36}$ dicarboxylic acids in cosmetics and/or pharmaceutical preparations. The compounds are characterized by a particularly light feeling.

9 Claims, No Drawings

COSMETIC COMPOSITIONS CONTAINING ESTERS OF 2-ETHYLBUTANOL

CROSS REFERENCE TO RELATED APPLICATIONS

This application is the National Phase entry of PCT/EP2007/007036, filed Aug. 9, 2007, which claims priority to EPO patent application number EP 06017218, filed Aug. 18, 2006, both of which are incorporated herein by reference in their entireties.

FIELD OF THE INVENTION

The invention relates to the use of esters of 2-ethylbutanol in cosmetic and/or pharmaceutical preparations, and to specific esters and processes for their preparation.

BACKGROUND OF THE INVENTION

In the area of cosmetic emulsions for skincare and hair care, a large number of requirements are imposed by the consumer: apart from the cleaning and care effects, which determine the intended use, value is placed on such differing parameters as highest possible dermatological compatibility, good refatting properties, elegant appearance, optimum sensory impression and storage stability.

Besides a series of surface-active substances, preparations which are used for the cleaning and care of the human skin and the hair generally comprise in particular oil bodies and water. The oil bodies/emollients used are, for example, hydrocarbons, ester oils, and vegetable and animal oils/fats/waxes. In order to meet the high market requirements with regard to sensory properties and optimum dermatological compatibility, new oil bodies and emulsifier mixtures are continuously being developed and tested. The use of ester oils in cosmetics has been known for a long time. On account of their importance, new processes for their preparation are also continuously being developed. In particular branched ester oils impart a "lighter" skin feel and are therefore being intensively investigated. The use of 2-methyl-1,3-propanediol monoesters is, for example, the subject of DE 101 60 681, the use of 2-methyl-1,3-propanediol esters is described in DE 101 60 682.

It was an object of the present invention to provide novel ester oils that are preferably liquid at 20° C. for cosmetic applications which have an improved profile with regard to the sensory properties (lightness, "nongreasy skin feel", softness, spreadability, absorption, distributability, oiliness) and can be incorporated into a large number of cosmetic formulations. In this connection, the hydrolysis stability of the esters and also the ability of the esters to be formulated at a low pH were also of interest. Furthermore, it should be possible to incorporate the esters both into W/O and also into O/W formulations. Furthermore, the esters should be compatible in particular with crystalline UV filters, pigments, antiperspirants salts and silicones. Surprisingly, it has been found that esters of 2-ethylbutanol lead to sensorily light products. Some of these esters are described by Wu, Y. et al., Huaxue Tongbao, 1985, (5), 19-24. Kano, T. et al. (2005) Jpn. Kokal Tokyo Koho (2005), 15 pp describe the use as environmentally friendly solvent for cleaning.

DETAILED DESCRIPTION OF PREFERRED EMBODIMENTS

The invention provides the use of esters of 2-ethylbutanol with C4-C36-carboxylic acids—or C4-C36-dicarboxylic acids, with the exception of the ester of 2-ethylbutanol with 2-methylpentanoic acid, in cosmetic preparations.

The invention provides the use of esters of 2-ethylbutanol with C4-C36-carboxylic acids—or C4-C36-dicarboxylic acids, with the exception of the diester of 2-ethylbutanol with hexanedicarboxylic acid, in pharmaceutical preparations.

The invention further provides the use of esters of 2-ethylbutanol with C4-C36-carboxylic acids—or C4-C36-dicarboxylic acids as oil bodies in cosmetic and/or pharmaceutical preparations.

Surprisingly, esters of 2-ethylbutanol are particularly well suited for cosmetic formulations, in particular for formulations for which a "light" skin feel is important. The esters can be very readily incorporated into various formulations. Depending on the chain length, branching and number of double bonds, liquid substance mixtures are obtained which are accordingly suitable as oil bodies or consistency regulators. According to the invention, it is possible to use a single 2-ethylbutyl C4-C36-carboxylic acid ester or 2-ethylbutyl C4-C36-dicarboxylic acid ester or any desired mixture.

The invention provides in particular the use of esters of 2-ethylbutanol with C4-C36-carboxylic acids—or C4-C36-dicarboxylic acids in cosmetic and/or pharmaceutical preparations for the wetting or impregnation or coating of utility wipes and/or hygiene wipes which are used for body cleaning and/or for body care.

In a preferred embodiment of the invention, esters are used whose total carbon number is less than or equal to 24, preferably less than or equal to 22.

According to the invention, preference is given to the use of esters of 2-ethylbutanol with carboxylic acids which are selected from the C4 to C30, in particular C6 to C24, in particular C6 to C22, in particular C6 to C18, in particular C8 to C18 preferably C8 to C16, preferably C8 to C12, in particular C6 to C10 carboxylic acids or the corresponding dicarboxylic acids.

Of suitability according to the invention for the use are esters of 2-ethylbutanol with C4 to C36, C5 to C30, C6 to C26, C7 to C24, C8 to C22, C9 to C20, C10 to C18, C11 to C17, C11 to C16, C12 to C15, C13 to C14 carboxylic acids or the corresponding dicarboxylic acids.

In a preferred embodiment of the invention, use is made of esters of 2-ethylbutanol with carboxylic acids which are selected from the C4 to C18 carboxylic acids, preferably C6 to C16 carboxylic acids, and also esters of 2-ethylbutanol with dicarboxylic acids which are selected from the C4 to C18 dicarboxylic acids, preferably C6 to C16 dicarboxylic acids.

In a particularly preferred embodiment of the invention, use is made of esters of 2-ethylbutanol with carboxylic acids selected from the C6 to C12 carboxylic acid, and also esters of 2-ethylbutanol with dicarboxylic acids selected from the C6 to C12 dicarboxylic acids.

The use of esters of 2-ethylbutanol with saturated carboxylic acids is preferred according to the invention. The use of esters of 2-ethylbutanol with saturated dicarboxylic acids is preferred according to the invention.

The use of esters of 2-ethylbutanol with linear, unbranched carboxylic acids is preferred according to the invention. The use of esters of 2-ethylbutanol with saturated dicarboxylic acids is preferred according to the invention.

The use of esters of 2-ethylbutanol with linear, unbranched carboxylic acid is preferred according to the invention.

The term "CX carboxylic acids" encompasses carboxylic acids with a total carbon number of X, thus e.g. "C8 carboxylic acids" encompasses all carboxylic acids which have a total carbon number of 8, such as, for example, n-octanoic acid, isooctanoic acids or methylheptanoic acids. Accordingly, the term "CX dicarboxylic acids" encompasses all acids with 2 carboxy groups which have a total carbon number of X, thus e.g. "C4 dicarboxylic acid" encompasses, inter alia, butanedioic acid (succinic acid) and also maleic acid and fumaric acid.

Within the context of the present invention, the term "carboxylic acid" refers to "monocarboxylic acids". The sensory testing of 2-ethylbutyl n-octanoate, 2-ethylbutyl n-decanoate and 2-ethylbutyl n-dodecanoate shows a significant improvement in the sensorics—in particular with regard to the spreading—compared with known emollients (e.g. various other ester oils or dialkyl carbonates).

Carboxylic acids which can be used are linear or branched, saturated or unsaturated, cyclic or acyclic or aromatic carboxylic acids.

Esters of 2-ethylbutanol with for example (trivial names of the acids in brackets) n-butanoic acid (butyric acid), 2-methylpropanoic acid (isobutyric acid), pentanoic acid (valeric acid), isopentanoic acid, such as, for example, 2,2-dimethylpropanoic acid (pivalic acid, neopentanoic acid) and 3-methylbutanoic acid (isopentanoic acid, isovaleric acid), hexanoic acid (caproic acid), heptanoic acid, octanoic acid (caprylic acid), isooctanoic acid such as e.g. in particular 2-ethylbutyl 2-ethylhexanoate, but also 2-ethylbutyl 3-ethylhexanoate, 2-ethylbutyl 4-ethylhexanoate, 2-ethylbutyl 5-ethylhexanoate, and technical-grade mixtures of branched octanoic acids, as are sold for example under the trade name Cekanoic® C8 by Exxon, are in accordance with the invention. Nonanoic acid (pelargonic acid, nonylic acid), decanoic acid (capric acid), isodecanoic acids, such as e.g. trimethylheptanoic acid (neodecanoic acid, isodecanoic acid), and technical-grade mixtures of branched decanoic acid, as are sold for example under the trade name Cekanoic® C10 by Exxon, undecanoic acid, undecenoic acid, dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), nonadecanoic acid, eicosanoic acid, docosanoic acid, tetracosanoic acid, hexacosanoic acid, dimer fatty acids (C36, as available for example under the trade name "Empol 1062" from Cognis), talc fatty acids, coconut fatty acids, palm fatty acids, ricinoleic acid, oleic acid, linoleic acid, linolenic acid, isostearic acid, isooctanoic acid, isononanoic acid, isodecanoic acid, 2-ethylhexanoic acid, 2-propyl-heptanoic acid, 2-butyloctanoic acid, 2-butyldecanoic acid, 2-hexyloctanoic acid, 2-hexyldecanoic acid, 2-hexyldodecanoic acid, 2-octyldecanoic acid, or dicarboxylic acids such as, for example, fumaric acid, maleic acid, adipic acid, pimelic acid, suberic acid, azelaic acid, sebacic acid. Also suitable are esters of 2-ethylbutanol with Cekanoic® C8 (isooctanoic acid), Cekanoic® C9 (isononanoic acid: 3,5,5-trimethylhexanoic acid and 2,5,5-trimethylhexanoic acid) and Cekanoic® C10 (isodecanoic acid) from Exxon Mobile, which are carboxylic acid isomer mixtures.

Esters of 2-ethylbutanol with aromatic carboxylic acids are in accordance with the invention. Aromatic carboxylic acids which can be specified are, for example, benzoic acid and/or benzoic acid derivatives.

Suitable benzoic acid derivatives are
mono- or polycarboxy-substituted benzoic acids, such as, for example, benzenedicarboxylic acids, such as 1,2-benzenedicarboxylic acid, 1,3-benzenedicarboxylic acid, 1,4-benzenedicarboxylic acid (terephthalic acid). These can optionally be alkyl- or hydroxyl-substituted.
mono- or polyalkyl-substituted benzoic acids, such as, for example, 2-methylbenzoic acid (=o-toluic acid), 3-methylbenzoic acid (=m-toluic acid), 4-methylbenzoic acid (=p-toluic acid), 2,4-dimethylbenzoic acid, 2-ethylbenzoic acid etc.
mono- or polyhydroxy-substituted benzoic acid, such as, for example, 2-hydroxybenzoic acid (salicylic acid), 3-hydroxybenzoic acid, 4-hydroxybenzoic acid, 2,4-dihydroxybenzoic acid
hydroxyl- and alkyl-substituted benzoic acids, such as, for example, 2-methyl-3-hydroxybenzoic acid
derivatives obtainable by acylation of hydroxy-substituted benzoic acids, such as, for example, acetylsalicylic acid.

In a preferred embodiment of the invention, the benzoic acid derivatives used are compounds selected from the group consisting of methyl-substituted benzoic acid, hydroxy-substituted benzoic acid, carboxy-substituted benzoic acid, derivatives obtainable by acylation of hydroxy-substituted benzoic acid.

By way of example, mention may be made of the esters of 2-ethylbutanol with benzoic acid, and the esters of 2-ethylbutanol with salicylic acid.

The term "esters of 2-ethylbutanol with dicarboxylic acids" encompasses both diesters of the dicarboxylic acids with 2-ethylbutanol, thus, for example, di-2-ethylbutyl n-octanedioic acid diester, and also monoesters, such as, for example, 2-ethylbutyl n-octanedioic acid monoester, and also mixed esters in which one acid group of the dicarboxylic acid has been esterified with 2-ethylbutanol and the second acid group of the dicarboxylic acid has been esterified with a further alcohol. A further embodiment of the invention encompasses mixed esters of dicarboxylic acids and 2-ethylbutanol and a further alcohol of the general formula R—OH, where R is a linear or branched, saturated or unsaturated alkyl radical having 1 to 12 carbon atoms.

In a further embodiment, mixed esters of dicarboxylic acids and 2-ethylbutanol and a further alcohol of the general formula R—OH, where R is a saturated, linear or branched, alkyl radical having 1 to 12 carbon atoms are used.

In a preferred embodiment, mixed esters of dicarboxylic acids and 2-ethylbutanol and a further alcohol, where the further alcohol is selected from the group consisting of methanol, ethanol, propanol, isopropanol, butanol, isobutanol, pentanol, hexanol, isohexanol, octanol, decanol or dodecanol are used.

In a preferred embodiment of the invention, esters of 2-ethylbutanol with C4 to C36 dicarboxylic acids, diesters and mixed esters are used.

The invention further provides esters of 2-ethylbutanol with carboxylic acids selected from C9 to C16 carboxylic acids. The invention encompasses both individual esters and also mixtures of different esters.

Esters of 2-ethylbutanol with saturated carboxylic acids are preferred according to the invention.

Esters of 2-ethylbutanol with linear, saturated carboxylic acids are preferred according to the invention.

One embodiment of the invention relates to esters of 2-ethylbutanol with branched carboxylic acids: within the context of the invention, the term "iso-acid" with X carbon atoms is to be understood as meaning all branched carboxylic acids which contain X carbon atoms in total. Thus, for example, methyl-, ethyl- or propyl-branched, optionally multibranched carboxylic acids. In a particular embodiment, the subgroup of the—optionally multi—methyl-branched carboxylic acids is used (=iso-acids).

The following esters are preferred: 2-ethylbutyl n-nonanoate, 2-ethylbutyl isononanoate, 2-ethylbutyl n-decanoate, 2-ethylbutyl isodecanoate, 2-ethylbutyl n-undecanoate, 2-ethylbutyl isoundecanoate, 2-ethylbutyl n-undecenoate, 2-ethylbutyl n-dodecanoate, 2-ethylbutyl isododecanoate, 2-ethylbutyl n-tridecanoate, 2-ethyl-butyl isotridecanoate, 2-ethylbutyl n-tetradecanoate, 2-ethylbutyl isotetradecanoate, 2-ethylbutyl n-penta-decanoate, 2-ethylbutyl isopentadecanoate, 2-ethylbutyl n-hexadecanoate, 2-ethylbutyl isohexadecanoate, 2-ethylbutyl benzoate.

The following esters are particularly preferred: 2-ethylbutyl n-nonanoate, 2-ethylbutyl isononanoate, 2-ethylbutyl n-decanoate, 2-ethylbutyl isodecanoate, 2-ethylbutyl n-dodecanoate, 2-ethylbutyl isododecanoate.

The invention provides 2-ethylbutyl n-nonanoate. The invention provides 2-ethylbutyl isononanoate. The invention provides 2-ethylbutyl n-decanoate. The invention provides 2-ethylbutyl isodecanoate. The invention provides 2-ethylbutyl n-undecanoate. The invention provides 2-ethylbutyl isoundecanoate. The invention provides 2-ethylbutyl n-undecenoate. The invention provides 2-ethylbutyl n-dodecanoate. The invention provides 2-ethylbutyl isododecanoate. The invention provides 2-ethylbutyl n-tridecanoate. The invention provides 2-ethylbutyl isotridecanoate. The invention provides 2-ethylbutyl n-tetradecanoate. The invention provides 2-ethylbutyl isotetradecanoate. The invention provides 2-ethylbutyl n-pentadecanoate. The invention provides 2-ethylbutyl isopentadecanoate. The invention provides 2-ethylbutyl n-hexadecanoate. The invention provides 2-ethylbutyl isohexadecanoate. The invention provides 2-ethylbutyl benzoate.

The invention further provides esters of 2-ethylbutanol with C5, C8, C11, C12, C14-C36-dicarboxylic acids or unsaturated C6, C7, C9, C10, C13-dicarboxylic acids. Of these, esters of 2-ethylbutanol with C9 to C16 dicarboxylic acids are preferred according to the invention. Of these, esters of 2-ethylbutanol with saturated dicarboxylic acids are preferred according to the invention. Of these, esters of 2-ethylbutanol with linear, saturated dicarboxylic acids are preferred according to the invention.

Surprisingly, it has been found that the esters are particularly suitable for use in cosmetic and/or pharmaceutical preparations.

Also provided is a process for the preparation of the esters according to the invention, where a mixture comprising 2-ethylbutanol and the corresponding acid is reacted.

Accordingly, the invention provides a process for the preparation of the esters, where a mixture comprising 2-ethylbutanol and at least one C9 to C16 carboxylic acid is reacted.

Accordingly, the invention provides a process for the preparation of the esters, where a mixture comprising 2-ethylbutanol and at least one C5, C8, C11, C12, C14-C36-dicarboxylic acids or unsaturated C6, C7, C9, C10, C13-dicarboxylic acids is reacted.

The process according to the invention likewise encompasses the preparation of ester mixtures in which 2-ethylbutanol is reacted with the corresponding acid mixtures.

The process according to the invention likewise encompasses the preparation of mixed esters of 2-ethylbutanol with at least one C4 to C36 dicarboxylic acid, in which a mixture of 2-ethylbutanol, at least one C4 to C36 dicarboxylic acid and at least one further alcohol of the general formula R—OH, where R is a saturated, linear or branched, alkyl radical having 1 to 12 carbon atoms, is reacted.

In a preferred embodiment of the invention, the mixture comprising alcohol and the corresponding acid is reacted with the addition of an esterification catalyst.

In a preferred embodiment, the mixture comprising alcohol and the corresponding acid is heated, the water which forms is continuously drawn off and the crude product is then distilled. The process can be carried out with the addition of an esterification catalyst, e.g. under acid catalysis or base catalysis. In a preferred embodiment, the process is carried out without the addition of solvents, preferably with starting materials which are as anhydrous as possible. In a preferred embodiment of the process, a tin catalyst is used. Suitable tin catalysts are, for example, tin oxalate (e.g. Fascat® 2001), tin oxide (SnO, Fascat® 2000), and also tin IV catalysts such as dibutyltin diacetate Fascat® 4200), dibutyltin oxide (Fascat® 4201), and dibutyltin laurate (Fascat® 4202) or tin oxide (SnO), which were formally marketed by Atofina and are currently marketed by Arkema.

Preferably, the esterification is carried out at temperatures between 100-300° C., in particular 200-250° C.

In a further embodiment, the catalyst used is at least one enzyme. Suitable enzymes are all enzymes or enzyme mixtures known to the person skilled in the art which are able to catalyze the esterification of alcohol and acid, examples which may be mentioned being lipases, acyl transferases and esterases. The enzymatically catalyzed esterification is usually carried out at temperatures of from 20 to 100° C., preferably 40 to 80° C.

The invention provides a process for the preparation of the esters according to the invention where a mixture comprising 2-ethylbutanol and the methyl ester of the corresponding acid is reacted with the addition of a transesterification catalyst.

The process according to the invention likewise encompasses the preparation of ester mixtures in which 2-ethylbutanol is reacted together with the corresponding mixtures of the methyl esters of the acids with the addition of a transesterification catalyst.

In a preferred embodiment, the mixture comprising alcohol and the methyl ester of the corresponding acid is heated with the addition of the esterification catalyst, the water which forms is continuously drawn off and the crude product is then distilled. In a preferred embodiment, the process is carried out without the addition of solvents, preferably with starting materials which are as anhydrous as possible.

Preferably, the esterification is carried out at temperatures between 100-300° C., in particular 200-250° C. Transesterification catalysts which may be used are all transesterification catalysts known to the person skilled in the art, preference being given to using sodium methylate or tetraalkyl titanate as transesterification catalyst.

In a further embodiment, the catalyst used is at least one enzyme. Suitable enzymes are all enzymes or enzyme mixtures known to the person skilled in the art which are able to catalyze the transesterification of alcohol and acid methyl ester, examples which may be mentioned being lipases, acyltransferases and esterases. The enzymatically catalyzed esterification is usually carried out at temperatures of from 20 to 100° C., preferably 40 to 80° C.

Cosmetic/Pharmaceutical Preparations

The 2-ethylbutyl esters permit the preparation of stable cosmetic and pharmaceutical emulsions with a particularly light skin feel.

The present invention therefore further provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b) at least one emulsifier and/or surfactant and/or wax component and/or polymer and/or a further oil body, with the exception of compositions which comprise di(2-ethylbutyl)hexanedioic acid diesters.

The present invention further provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b) at least one emulsifier and/or surfactant and/or wax component and/or polymer and/or a further oil body,
with the exception of compositions which comprise di(2-ethylbutyl)hexanedioic diesters and with the exception of compositions which comprise an ester of 2-ethylbutanol with 2-methylpentanoic acid.

The present invention provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b-1) at least one emulsifier.

The present invention provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b-2) at least one surfactant,
with the exception of compositions which comprise di(2-ethylbutyl)hexanedioic acid diesters.

The present invention provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b-3) at least one wax component.

The present invention provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b-4) at least one polymer.

The present invention provides cosmetic and/or pharmaceutical preparations comprising
a) at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b-5) at least one further oil body.

Preferably, the preparations according to the invention comprise 0.1 to 80% by weight, in particular 0.5 to 70% by weight, preferably 0.75 to 60% by weight, in particular 1 to 50% by weight, preferably 1-40% by weight, of at least one ester of 2-ethylbutanol with C4-C36-carboxylic acids—or C4-C36-dicarboxylic acids.

The invention further provides preparations cosmetic and/or pharmaceutical preparations comprising
a) 0.1-80% by weight, in particular 0.1 to 70% by weight, preferably 0.1 to 60% by weight, in particular 0.1 to 50% by weight, preferably 0.1-40% by weight, of at least one ester of 2-ethylbutanol with C4-C36-carboxylic acids—or C4-C36-dicarboxylic acids, preferably at least one ester of 2-ethylbutanol with C4-C18-carboxylic acids—or C4-C18-dicarboxylic acids
b) 0.1-20% by weight of emulsifier (b-1) and/or surfactant (b-2) and/or wax component (b-3) and/or polymer (b-4)
b-5) 0.1-40% by weight of further oil bodies and
c) 0-98% by weight of water.

The preparations according to the invention comprise at least 0.1, in particular at least 0.5, in particular at least 0.75, preferably at least 1, preferably at least 5, % by weight of one or more esters (a).

All of the % by weight data refer to % by weight based on the cosmetic and/or pharmaceutical preparation.

In a preferred embodiment of the invention, the preparations comprise esters whose total carbon number is less than or equal to 24, preferably less than or equal to 22.

In a preferred embodiment, the preparations comprise at least one ester of 2-ethylbutanol with C4-C36-carboxylic acids—or an ester of 2-ethylbutanol with C5, C8, C11, C12, C14-C36-dicarboxylic acids or unsaturated C6, C7, C9, C10, C13-dicarboxylic acids.

The preparations according to the invention preferably comprise esters of 2-ethylbutanol with carboxylic acids which are selected from the C4 to C30, in particular C6 to C24, in particular C6 to C22, in particular C6 to C18, in particular C8 to C18, preferably C8 to C16, preferably C8 to C12, in particular C6 to C10, carboxylic acids or the corresponding dicarboxylic acids.

Of suitability according to the invention for the preparations according to the invention are esters of 2-ethylbutanol with C4 to C36, C5 to C30, C6 to C26, C7 to C24, C8 to C22, C9 to C20, C10 to C18, C11 to C17, C11 to C16, C12 to C15, C13 to C14 carboxylic acids or the corresponding dicarboxylic acids.

In a preferred embodiment of the invention, the preparations according to the invention comprise esters of 2-ethylbutanol with carboxylic acids which are selected from the C4 to C18 carboxylic acids, preferably C6 to C16 carboxylic acids, and esters of 2-ethylbutanol with dicarboxylic acids which are selected from the C4 to C18 dicarboxylic acids, preferably C6 to C16 dicarboxylic acids.

In a particularly preferred embodiment of the invention, the preparations according to the invention comprise esters of 2-ethylbutanol with carboxylic acids which are selected from the C6 to C12 carboxylic acids, and also esters of 2-ethylbutanol with dicarboxylic acids which are selected from the C6 to C12 dicarboxylic acids.

Within the context of the invention, preference is given to preparations which comprise esters of 2-ethylbutanol with C6-C16-, preferably from the C6-C12-carboxylic acids or the corresponding dicarboxylic acids. Among these, linear, unbranched carboxylic acids are preferred. Particular preference is given to cosmetic compositions with 2-ethylbutyl caprylate, 2-ethylbutyl capronate, 2-ethylbutyl caprinate and/or 2-ethylbutyl laurate.

The preparations according to the invention preferably comprise esters of 2-ethylbutanol with saturated carboxylic acids. The preparations according to the invention preferably comprise esters of 2-ethylbutanol with saturated dicarboxylic acids.

The use of esters of 2-ethylbutanol with linear, unbranched carboxylic acids is preferred according to the invention. The use of esters of 2-ethylbutanol with linear, unbranched dicarboxylic acids is preferred according to the invention.

The preparations according to the invention can comprise both individual esters and also mixtures of different esters.

In a preferred embodiment of the invention, the preparations comprise at least one ester of 2-ethylbutanol with C8 to C16 carboxylic acids.

In a preferred embodiment of the invention, the preparations comprise at least one ester of 2-ethylbutanol with C5, C8, C11, C12, C14-C36-dicarboxylic acids or unsaturated C6, C7, C9, C10, C13-dicarboxylic acids.

In a preferred embodiment of the invention, the preparations comprise at least one ester of 2-ethylbutanol with C8 to C12 carboxylic acids.

In a preferred embodiment of the invention, the preparations comprise at least one ester selected from the group consisting of 2-ethylbutyl n-nonanoate, 2-ethylbutyl isononanoate, 2-ethylbutyl n-decanoate, 2-ethylbutyl isodecanoate, 2-ethylbutyl n-undecanoate, 2-ethylbutyl isoundecanoate, 2-ethylbutyl n-undecenoate, 2-ethylbutyl n-dodecanoate, 2-ethylbutyl isododecanoate, 2-ethylbutyl n-tridecanoate, 2-ethylbutyl isotridecanoate, 2-ethylbutyl n-tetradecanoate, 2-ethylbutyl isotetradecanoate, 2-ethylbutyl n-pentadecanoate, 2-ethylbutyl isopentadecanoate, 2-ethylbutyl n-hexadecanoate, 2-ethylbutyl isohexadecanoate, 2-ethylbutyl benzoate or mixtures thereof.

In a preferred embodiment of the invention, the preparations comprise at least one ester selected from the group consisting of 2-ethylbutyl n-octanoate, 2-ethylbutyl isooctanoate, 2-ethylbutyl n-nonanoate, 2-ethylbutyl isononanoate, 2-ethylbutyl n-decanoate, 2-ethylbutyl isodecanoate, 2-ethylbutyl n-undecanoate, 2-ethylbutyl isoundecanoate, 2-ethylbutyl n-un-decenoate, 2-ethylbutyl n-dodecanoate, 2-ethylbutyl isododecanoate, 2-ethylbutyl n-tridecanoate, 2-ethyl-butyl isotridecanoate, 2-ethylbutyl n-tetradecanoate, 2-ethylbutyl isotetradecanoate, 2-ethylbutyl n-penta-decanoate, 2-ethylbutyl isopentadecanoate, 2-ethylbutyl n-hexadecanoate, 2-ethylbutyl isohexadecanoate or mixtures thereof.

In a preferred embodiment of the invention, the preparations comprise at least one ester selected from the group consisting of 2-ethylbutyl n-octanoate, 2-ethylbutyl isooctanoate, 2-ethylbutyl n-nonanoate, 2-ethylbutyl isononanoate, 2-ethylbutyl n-decanoate, 2-ethylbutyl isodecanoate, 2-ethylbutyl n-dodecanoate, 2-ethylbutyl isododecanoate or mixtures thereof.

A further preferred embodiment of the cosmetic and/or pharmaceutical preparations comprises (a) 0.1-80% by weight, in particular 0.1 to 70% by weight, preferably 0.1 to 60% by weight, preferably 0.1 to 50% by weight, of at least one ester of 2-ethylbutanol with C4-C36-carboxylic acids—or C4-C36-dicarboxylic acids, (b) 0.1-20% by weight of emulsifiers (b-1) and/or surfactants (b-2) and/or wax components (b-3) and/or polymers (b-4), and 0.1-40% by weight of further oil bodies (b-5) and (d) 0-98% by weight of water.

The term "esters of 2-ethylbutanol with dicarboxylic acids" encompasses both esters of dicarboxylic acids with 2-ethylbutanol, thus, for example, di-2-ethylbutyl n-octanedioic acid diester, and also monoesters, such as, for example, 2-ethylbutyl n-octanedioic acid monoester, and also mixed esters in which one acid group of the dicarboxylic acid has been esterified with 2-ethylbutanol and the second acid group of the dicarboxylic acid has been esterified with a further alcohol.

In a further embodiment, mixed esters of dicarboxylic acids and 2-ethylbutanol and a further alcohol of the general formula R—OH, where R is a linear or branched, saturated or unsaturated alkyl radical having 1 to 12 carbon atoms are used.

In a further embodiment, mixed esters of dicarboxylic acids and 2-ethylbutanol and a further alcohol of the general formula R—OH, where R is a saturated, linear or branched, alkyl radical having 1 to 12 carbon atoms, are used.

In a preferred embodiment, mixed esters of dicarboxylic acids and 2-ethylbutanol and a further alcohol, where the further alcohol is selected from the group consisting of methanol, ethanol, propanol, isopropanol, butanol, isobutanol, pentanol, hexanol, isohexanol, octanol, decanol or dodecanol, are used.

In a preferred embodiment of the invention, the esters of 2-ethylbutanol with C4 to C36 dicarboxylic acids used are diesters and mixed esters.

In a preferred embodiment, the preparations according to the invention comprise esters of 2-ethylbutanol with linear, branched, saturated or unsaturated C4 to C32 dicarboxylic acids, in particular C4 to C30, in particular C6 to C24, in particular C6 to C22, in particular C8 to C18, in particular C8 to C16, preferably C8 to C16, preferably C8 to C12 dicarboxylic acids.

Of suitability according to the invention for the preparations according to the invention are esters of 2-ethylbutanol with C4 to C36, C5 to C30, C6 to C26, C7 to C24, C8 to C22, C9 to C20, C10 to C18, C11 to C17, C11 to C16, C12 to C15, C13 to C14 dicarboxylic acids.

In a particularly preferred embodiment of the invention, the preparations comprise esters of 2-ethylbutanol with dicarboxylic acids which are selected from the C6 to C12 dicarboxylic acids.

In a particularly preferred embodiment of the invention, the preparations comprise esters of 2-ethylbutanol with C5, C8, C11, C12, C14-C36-dicarboxylic acids or unsaturated C6, C7, C9, C10, C13-dicarboxylic acids.

Esters of 2-ethylbutanol with saturated dicarboxylic acids are preferred according to the invention.

Esters of 2-ethylbutanol with linear, unbranched dicarboxylic acids are preferred according to the invention.

Suitable diesters of the dicarboxylic acids of 2-ethylbutanol are di-2-ethylbutyl n-butanedioic acid diester, di-2-ethylbutyl isobutanedioic acid diester, di-2-ethylbutyl n-pentanedioic acid diester, di-2-ethylbutyl isopentanedioic acid diester, di-2-ethylbutyl n-hexanedioic acid diester, di-2-ethylbutyl isohexanedioic acid diester, di-2-ethylbutyl n-heptanedioic acid diester, di-2-ethylbutyl isoheptanedioic acid diester, di-2-ethylbutyl n-octanedioic acid diester, di-2-ethylbutyl isooctanedioic acid diester, di-2-ethylbutyl n-nonanedioic acid diester, di-2-ethylbutyl isononanedioic acid diester, di-2-ethylbutyl n-decanedioic acid diester, di-2-ethylbutyl isodecanedioic acid diester, di-2-ethylbutyl n-undecanedioic acid diester, di-2-ethylbutyl isoundecanedioic acid diester, di-2-ethylbutyl n-undecenedioic acid diester, di-2-ethylbutyl isoundecenedioic acid diester, di-2-ethylbutyl n-dodecanedioic acid diester, di-2-ethylbutyl isododecanedioic acid diester.

Suitable mixed esters of dicarboxylic acids of 2-ethylbutanol and methanol are 2-ethylbutyl methyl n-butanedioic acid diester, 2-ethylbutyl methyl isobutanedioic acid diester, 2-ethylbutyl methyl n-pentanedioic acid diester, 2-ethylbutyl methyl isopentanedioic acid diester, 2-ethylbutyl methyl n-hexanedioic acid diester, 2-ethylbutyl methyl isohexanedioic acid diester, 2-ethylbutyl methyl n-heptanedioic acid diester, 2-ethylbutyl methyl isoheptanedioic acid diester, 2-ethylbutyl methyl n-octanedioic acid diester, 2-ethylbutyl methyl isooctanedioic acid diester, 2-ethylbutyl methyl n-nonanedioic acid diester, 2-ethylbutyl methyl isononanedioic acid diester, 2-ethylbutyl methyl n-decanedioic acid diester, 2-ethylbutyl methyl isodecanedioic acid diester, 2-ethylbutyl methyl n-undecanedioic acid diester, 2-ethylbutyl methyl isoundecanedioic acid diester, 2-ethylbutyl methyl n-undecenedioic acid diester, 2-ethylbutyl methyl isoundecenedioic acid diester, 2-ethylbutyl methyl n-dodecanedioic acid diester, 2-ethylbutyl methyl isododecanedioic acid diester.

Corresponding mixed esters of dicarboxylic acids of 2-ethylbutanol and at least one further alcohol of the general formula R—OH, where R is a linear or branched, saturated or unsaturated alkyl radical having 1 to 12 carbon atoms, are likewise encompassed.

In particular, corresponding mixed esters of dicarboxylic acids of 2-ethylbutanol and at least one further alcohol are encompassed, where the further alcohol selected from the group consisting of ethanol, propanol, isopropanol, butanol, isobutanol, pentanol, hexanol, isohexanol, octanol, decanol or dodecanol.

The invention provides esters of 2-ethylbutanol with dimer fatty acids. The term "dimer fatty acids" refers to polycarboxylic acids which are obtained by polymerization of unsaturated fatty acids, primarily of oleic acid or of tall oil fatty acid. Commercial dimer fatty acids consist of a mixture which, besides small fractions of linear and branched C18 monocarboxylic acids (monomer fatty acid), comprises predominantly C36 dicarboxylic acid and varying fractions of C54 tricarboxylic acid (trimer fatty acid) as well as traces of higher polymeric fatty acids.

The preparations according to the invention, the compositions according to the invention and the esters according to the invention are suitable to be incorporated as a base in all cosmetic compositions for body care and body cleansing, such as, for example, body oil, baby oil, body milk, creams, lotions, sprayable emulsions, sunscreen compositions, antiperspirants, liquid soaps and bar soaps etc. They can also be used in surfactant-containing formulations, such as, for example, foam and shower baths, hair shampoos and care rinses. They can be applied as care component on tissues, papers, wipes, fleece products, sponges, puffs, plasters and bandages, which are used in the sector of hygiene and care (wet wipes for baby hygiene and baby care, cleansing wipes, face cleansing wipes, skincare wipes, care wipes with active ingredients to combat skin aging, wipes with sunscreen formulations and insect repellants, and also wipes for decorative cosmetics or for aftersun treatment, toilet wet wipes, antiperspirant wipes, diapers, tissues, wet wipes, hygiene products, self-tanning wipes). They can also be used, inter alia, in preparations for hair care, hair cleansing or hair coloring.

Depending on the application purpose, the cosmetic formulations comprise a series of further auxiliaries and additives, such as, for example, surfactants, further oil bodies, emulsifiers, pearlescent waxes, consistency regulators, thickeners, superfatting agents, stabilizers, polymers, fats, waxes, lecithins, phospholipids, biogenic active ingredients, UV photoprotective factors, antioxidants, deodorants, antiperspirants, antidandruff agents, film formers, swelling agents, insect repellants, self-tanning agents, tyrosinase inhibitors (depigmentation agents), hydrotropes, solubilizers, preservatives, perfume oils, dyes etc., which are listed below by way of example.

Emulsifier b-1)

In one embodiment of the invention, the preparations according to the invention comprise at least one emulsifier. The compositions according to the invention comprise the emulsifier(s) in an amount of from 0 to 40% by weight, preferably 0.1 to 20% by weight, preferably 0.1 to 15% by weight and in particular 0.1 to 10% by weight, based on the total weight of the composition.

In one embodiment of the invention, the preparation according to the invention comprises more than one emulsifier. The person skilled in the art uses customary emulsifier systems (such as, for example, emulsifier and coemulsifier) depending on the other components.

Nonionic Emulsifiers

The group of nonionic emulsifiers includes, for example:

(1) Addition products from 2 to 50 mol of ethylene oxide and/or 1 to 20 mol of propylene oxide onto linear fatty alcohols having 8 to 40 carbon atoms, onto fatty acids having 12 to 40 carbon atoms and onto alkylphenols having 8 to 15 carbon atoms in the alkyl group.

(2) $C_{12}$-$C_{18}$-fatty acid mono- and diesters of addition products of from 1 to 50 mol of ethylene oxide onto glycerol.

(3) Sorbitan mono- and diesters of saturated and unsaturated fatty acids having 6 to 22 carbon atoms and ethylene oxide addition products thereof.

(4) Alkyl mono- and oligoglycosides having 8 to 22 carbon atoms in the alkyl radical and their ethoxylated analogs.

(5) Addition products of from 7 to 60 mol of ethylene oxide onto castor oil and/or hydrogenated castor oil.

(6) Polyol and in particular polyglycerol esters, such as, for example, polyol poly-12-hydroxystearates, polyglycerol polyricinoleate, polyglycerol diisostearate or polyglycerol dimerate. Likewise suitable are mixtures of compounds from two or more of these substance classes.

(7) Addition products of from 2 to 15 mol of ethylene oxide onto castor oil and/or hydrogenated castor oil.

(8) Partial esters based on linear, branched, unsaturated or saturated $C_6$-$C_{22}$-fatty acids, ricinoleic acid, and 12-hydroxystearic acid and polyglycerol, pentaerythritol, dipentaerythritol, sugar alcohols (e.g. sorbitol), alkyl glucosides (e.g. methyl glucoside, butyl glucoside, lauryl glucoside), and also polyglucosides (e.g. cellulose), or mixed esters, such as, for example, glyceryl stearate citrate and glyceryl stearate lactate.

(9) Polysiloxane-polyalkyl-polyether copolymers and corresponding derivatives.

(10) Mixed esters of pentaerythritol, fatty acids, citric acid and fatty alcohol and/or mixed esters of fatty acids having 6 to 22 carbon atoms, methylglucose and polyols, preferably glycerol or polyglycerol.

The addition products of ethylene oxide and/or of propylene oxide onto fatty alcohols, fatty acids, alkylphenols, glycerol mono- and diesters, and also sorbitan mono- and diesters of fatty acids or onto castor oil are known, commercially available products. These are homolog mixtures whose average degree of alkoxylation corresponds to the ratio of the quantitative amounts of ethylene oxide and/or propylene oxide and substrate with which the addition reaction is carried out. Depending on the degree of ethoxylation, they are W/O or O/W emulsifiers. $C_{12/18}$-fatty acid mono- and diesters of addition products of ethylene oxide onto glycerol are known as refatting agents for cosmetic preparations.

Particularly highly suitable and mild emulsifiers according to the invention are polyol poly-12-hydroxystearates and mixtures thereof, which are sold, for example, under the names "Dehymuls® PGPH" (W/O emulsifier) or "Eumulgin® VL 75" (mixture with coco glucosides in the weight ratio 1:1, O/W emulsifier) or Dehymuls® SBL (W/O emulsifier) from Cognis Deutschland GmbH. In this connection, reference may be made in particular to the European Patent EP 0 766 661 B1. The polyol component of these emulsifiers can be derived from substances which have at least two, preferably 3 to 12 and in particular 3 to 8, hydroxyl groups and 2 to 12 carbon atoms.

Suitable lipophilic W/O emulsifiers are in principle emulsifiers with an HLB value of from 1 to 8, which are summarized in numerous tables and are known to the person skilled in the art. Some of these emulsifiers are listed, for example, in Kirk-Othmer, "Encyclopedia of Chemical Technology", 3rd edition, 1979, volume 8, page 913. For ethoxylated products, the HLB value can also be calculated according to the following formula: HLB=(100−L): 5, where L is the weight fraction of the lipophilic groups, i.e. of the fatty alkyl or fatty acyl groups in percent by weight, in the ethylene oxide adducts.

From the group of W/O emulsifiers, partial esters of polyols, in particular of $C_4$-$C_6$-polyols, such as, for example, partial esters of pentaerythritol or sugar esters, e.g. saccharose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof are particularly advantageous. Suitable emulsifiers are also addition products of from 1 to 30, preferably 5 to 10 mol of ethylene oxide onto the specified sorbitan esters.

Depending on the formulation, it may be advantageous to additionally use at least one emulsifier from the group of nonionic O/W emulsifiers (HLB value: 8-18) and/or solubilizers. These are, for example, the ethylene oxide adducts already mentioned in the introduction which have a correspondingly high degree of ethoxylation, e.g. 10-20 ethylene oxide units for O/W emulsifiers and 20-40 ethylene oxide units for so-called solubilizers. According to the invention, particularly advantageous O/W emulsifiers are Ceteareth-12 and PEG-20 stearate. Suitable solubilizers are preferably Eumulgin® HRE 40 (INCI: PEG-40 hydrogenated castor oil), Eumulgin® HRE 60 (INCI: PEG-60 hydrogenated castor oil), Eumulgin® L (INCI: PPG-1-PEG-9 lauryl glycol ether), and also Eumulgin® SML 20 (INCI: Polysorbate-20).

Nonionic emulsifiers from the group of alkyl oligoglycosides are particularly skin-friendly and therefore preferably suitable as O/W emulsifiers. $C_8$-$C_{22}$-Alkyl mono- and oligoglycosides, their preparation and their use are known from the prior art. Their preparation takes place in particular by reacting glucose or oligosaccharides with primary alcohols having 8 to 22 carbon atoms. With regard to the glucoside radical, both monoglycosides, in which one cyclic sugar radical is glycosidically bonded to the fatty alcohol, and also oligomeric glycosides with a degree of oligomerization up to preferably about 8 are suitable. The degree of oligomerization here is a statistical average value which is based on a homolog distribution customary for such technical products.

Products which are available under the name Plantacare® comprise a glucosidically bonded $C_8$-$C_{16}$-alkyl group on an oligoglucoside radical whose average degree of oligomerization is 1 to 2. The acyl glucamides derived from glucamine are also suitable as nonionic emulsifiers. According to the invention, preference is given to a product which is sold under the name Emulgade® PL 68/50 by Cognis Deutschland GmbH and is a 1:1 mixture of alkyl polyglucosides and fatty alcohols. According to the invention, a mixture of lauryl glucoside, polyglycerol-2 dipolyhydroxystearate, glycerol and water, which is commercially available under the name Eumulgin® VL 75, can also be used advantageously.

Suitable emulsifiers are also substances such as lecithins and phospholipids. Examples of natural lecithins which may be mentioned are the cephalins, which are also referred to as phosphatidic acids and are derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines and/or sphingolipids are also suitable.

Surfactants b-2)

In one embodiment of the invention, the preparations according to the invention comprise at least one surfactant. Surface-active substances which may be present are anionic, nonionic, cationic and/or amphoteric or zwitterionic surfactants. In surfactant-containing cosmetic preparations, such as, for example, shower gels, foam baths, shampoos etc., at least one anionic surfactant is preferably present.

The compositions according to the invention comprise the surfactant(s) in an amount of from 0 to 40% by weight, preferably 0 to 20% by weight, preferably 0.1 to 15% by weight and in particular 0.1 to 10% by weight, based on the total weight of the composition.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolyzates (in particular wheat-based vegetable products), polyol fatty acid esters, sugar esters, sorbitan esters, polysorbates and amine oxides. If the nonionic surfactants comprise polyglycol ether chains, these can have a conventional homolog distribution, but preferably have a narrowed homolog distribution.

Zwitterionic surfactants is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxylmethyl-3-hydroxyethylimidazoline having in each case 8 to 18 carbon atoms in the alkyl or acyl group, and cocoacylaminoethyl-hydroxyethylcarboxymethyl glycinate. A preferred zwitterionic surfactant is the fatty acid amide derivative known under the INCI name Cocamidopropyl Betaine.

Likewise suitable, particularly as cosurfactants, are ampholytic surfactants. Ampholytic surfactants are understood as meaning those surface-active compounds which, apart from a $C_8$-$C_{18}$-alkyl or acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkyl-amidopropylglycines, N-alkyltaurines, N-alkyl-sarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

Anionic surfactants are characterized by a water-solubilizing, anionic group such as, for example, a carboxylate, sulfate, sulfonate or phosphate group and a lipophilic radical. Skin-compatible anionic surfactants are known to the person skilled in the art in a large number from relevant handbooks and are commercially available. These are in particular alkyl sulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and sulfosuccinates and acyl glutamates in the form of their alkali metal or ammonium salts.

Cationic surfactants which can be used are in particular quaternary ammonium compounds. Preference is given to ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Furthermore, the very readily biodegradable quaternary ester compounds, such as, for example, the dialkylammonium methosulfates and methyl-hydroxyalkyldialkoyloxyalkylammonium methosulfates sold under the trade name Stepantex® and the corresponding products of the Dehyquart® series, can be used as cationic surfactants. The term "ester quats" is generally understood as meaning quaternized fatty acid triethanolamine ester salts. They can impart a particular soft feel to the compositions according to the invention. These are known substances which are prepared by the relevant methods of organic chemistry. Further cationic surfactants that can be used according to the invention are the quaternized protein hydrolyzates.

Wax Component b-3)

In one embodiment of the invention, the preparations according to the invention comprise at least one wax component. The compositions according to the invention comprise the wax component(s) in an amount of from 0 to 40% by weight, in particular from 0 to 20% by weight, preferably 0.1 to 15% by weight and in particular 0.1 to 10% by weight, based on the total weight of the composition.

The term wax is generally understood as meaning all natural or synthetically obtained substances and substance mixtures with the following properties: they are of solid to brittly hard consistency, coarse to finely crystalline, transparent to opaque and melt above 30° C. without decomposition. Even a little above the melting point, they are of low viscosity and not thread-drawing and exhibit a highly temperature-dependent consistency and solubility. According to the invention, it is possible to use a wax component or a mixture of wax components which melt at 30° C. or above.

According to the invention, waxes which can be used are also fats and fat-like substances with wax-like consistency provided they have the required melting point. These include, inter alia, fats (triglycerides), mono- and diglycerides, natural and synthetic waxes, fatty alcohols and wax alcohols, fatty acids, esters of fatty alcohols and fatty acids, and fatty acid amides or any desired mixtures of these substances.

Fats are understood as meaning triacylglycerols, i.e. the triple esters of fatty acids with glycerol. Preferably, they comprise saturated, unbranched and unsubstituted fatty acid radicals. These may be mixed esters, i.e. triple esters of glycerol with various fatty acids. So-called hydrogenated fats and oils obtained by partial hydrogenation can be used according to the invention and are particularly suitable as consistency regulators. Vegetable hydrogenated fats and oils are preferred, e.g. hydrogenated castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat.

Inter alia, the triple esters of glycerol with C12-C60-fatty acids and in particular C12-C36-fatty acids are suitable. These include hydrogenated castor oil, a triple ester of glycerol and a hydroxystearic acid, which is commercially available, for example, under the name Cutina HR. Glycerol tristearate, glycerol tribehenate (e.g. Syncrowax HRC), glycerol tripalmitate or the triglyceride mixtures known under the name Syncrowax HGLC are likewise suitable, with the proviso that the melting point of the wax component or of the mixture is 30° C. or above.

According to the invention, wax components which can be used are in particular mono- and diglycerides and mixtures of these partial glycerides. Glyceride mixtures that can be used according to the invention include the products Novata AB and Novata B (mixture of C12-C18-mono-, di- and triglycerides) and Cutina MD or Cutina GMS (glycerol stearate) marketed by Cognis Deutschland GmbH & Co. KG.

Fatty alcohols which can be used according to the invention as wax component include the C12-C50-fatty alcohols. The fatty alcohols can be obtained from natural fats, oils and waxes, such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated, unbranched fatty alcohols are preferred. However, unsaturated, branched or unbranched fatty alcohols can also be used according to the invention as wax component provided they have the required melting point. According to the invention, it is also possible to use fatty alcohol cuts as are produced during the reduction of naturally occurring fats and oils, such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut fat. However, it is also possible to use synthetic alcohols, e.g. the linear, even-numbered fatty alcohols of the Ziegler synthesis (alfols) or the partially branched alcohols from the oxo synthesis (dobanols). According to the invention, C14-C22-fatty alcohols, which are marketed, for example, by Cognis Deutschland GmbH under the name Lanette 16 (C16-alcohol), Lanette 14 (C14-alcohol), Lanette O (C16/C18-alcohol) and Lanette 22 (C18/C22-alcohol) are particularly preferably suitable. Fatty alcohols give the compositions a drier skin feel than triglycerides and are therefore preferred over the latter.

Wax components which can be used are also C14-C40-fatty acids or mixtures thereof. These include, for example, myristic acid, pentadecanoic acid, palmitic acid, margaric acid, stearic acid, nonadecanoic acid, arachic acid, behenic acid, lignoceric acid, cerotic acid, mellissic acid, erucic acid and elaeostearic acid, and substituted fatty acids, such as, for example, 12-hydroxystearic acid, and the amides or monoethanolamides of the fatty acids, this list being exemplary and nonlimiting in character.

According to the invention, it is possible to use, for example, natural vegetable waxes, such as candelilla wax, carnauba wax, japan wax, esparto grass wax, cork wax, guaruma wax, rice germ oil wax, sugar cane wax, ouricury wax, montan wax, sunflower wax, fruit waxes such as orange waxes, lemon waxes, grapefruit wax, bayberry wax, and animal waxes, such as, for example, beeswax, shellac wax, spermaceti, wool wax and uropygial fat. Within the context of the invention, it may be advantageous to use hydrogenated or hardened waxes. Natural waxes that can be used according to the invention also include the mineral waxes, such as, for example, ceresin and ozokerite or the petrochemical waxes, such as, for example, petrolatum, paraffin waxes and microwaxes. Wax components which can be used are also chemically modified waxes, in particular the hard waxes, such as, for example, montan ester waxes, sasol waxes and hydrogenated jojoba waxes. Synthetic waxes which can be used according to the invention include, for example, wax-like polyalkylene waxes and polyethylene glycol waxes. Vegetable waxes are preferred according to the invention.

The wax component can likewise be selected from the group of wax esters of saturated and/or unsaturated, branched and/or unbranched alkane carboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of lactides of long-chain hydroxycarboxylic acids. Examples of such esters are the C16-C40-alkyl stearates, C20-C40-alkyl stearates (e.g. Kesterwachs K82H), C20-C40-dialkyl esters of dimer acids, C18-C38-alkylhydroxystearoyl stearates or C20-C40-alkyl erucates. C30-C50-Alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate can also be used.

Polymers b-4)

In one embodiment of the invention, the preparations according to the invention comprise at least one polymer. The compositions according to the invention comprise the polymer(s) in an amount of from 0 to 20% by weight, preferably 0.1 to 15% by weight and in particular 0.1 to 10% by weight, based on the total weight of the composition.

Suitable cationic polymers are, for example, cationic cellulose derivatives, such as, for example, a quaternized hydroxyethylcellulose which is available under the name Polymer JR 400® from Amerchol, cationic starch, copolymers of diallylammonium salts and acrylamides, quaternized vinylpyrrolidone/vinylimidazole polymers, such as, for example, Luviquat® (BASF), condensation products of polyglycols and amines, quaternized collagen polypeptides, such as, for example, lauryldimonium hydroxypropyl hydrozyled collagen (Lamequat® L/Grünau), quaternized wheat polypeptides, polyethyleneimine, cationic silicone polymers, such as, for example, amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides, cationic chitin derivatives, such as, for example, quaternized chitosan, optionally in microcrystalline distribution, condensation products of dihaloalkylene, such as, for example, dibromobutane with bisdialkylamines, such as, for example, bis-dimethylamino-1,3-propane, cationic guar gum, such as, for example Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobronyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropyl methacylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Suitable polymers are likewise polysaccharides, in particular xanthan gum, guar-guar, agar-agar, alginates and tyloses.

Further Oil Bodies b-5)

Body care compositions such as creams, body oils, lotions and milks usually comprise a series of further oil bodies and emollients which contribute to further optimizing the sensory properties. The oil bodies (esters according to the invention plus further oil bodies) are usually present in a total amount of 0.1-80% by weight, in particular 0.5 to 70% by weight, preferably 1 to 60% by weight, in particular 1 to 50% by weight, in particular 1 to 40% by weight, preferably 5-25% by weight and in particular 5-15% by weight. The further oil bodies are usually present in an amount of from 0.1 to 40% by weight.

Suitable further oil bodies are, for example, Guerbet alcohols based on fatty alcohols having 6 to 18, preferably 8 to 10, carbon atoms, and also further additional esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Likewise suitable are esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol), triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols and hydrocarbons or mixtures thereof (Cetiol® DD).

Further Ingredients

Suitable thickeners are, for example, Aerosil grades (hydrophilic silicas), carboxymethylcellulose and hydroxyethyl- and hydroxypropylcellulose, polyvinyl alcohol, polyvinylpyrrolidone and bentonites such as, for example, Bentone® Gel VS-5PC (Rhoex).

UV photoprotective factors are to be understood, for example, as meaning organic substances (photoprotective filters) which are present in crystalline or liquid form at room temperature and which are able to absorb ultraviolet rays and release the absorbed energy again in the form of longer-wave radiation, e.g. heat. UV-B filters may be oil-soluble or water-soluble. Suitable typical UV-A filters are in particular derivatives of benzoylmethane. The UV-A and UV-B filters may of course also be used in mixtures, e.g. combinations of the derivatives of benzoylmethane, e.g. 4-tert-butyl-4'-methoxy-dibenzoylmethane (Parsol® 1789) and 2-ethylhexyl 2-cyano-3,3-phenylcinnamate (octocrylene), and esters of cinnamic acid, preferably 2-ethylhexyl 4-methoxycinnamate and/or propyl 4-methoxycinnamate and/or isoamyl 4-methoxycinnamate. Such combinations are often combined with water-soluble filters such as, for example, 2-phenylbenzimidazole-5-sulfonic acid and its alkali metal, alkaline earth metal, ammonium, alkylammonium, alkanolammonium and glucammonium salts.

Besides the specified soluble substances, insoluble photoprotective pigments, namely finely disperse metal oxides, are also suitable. Examples of suitable metal oxides are in particular zinc oxide and titanium dioxide. Besides the two aforementioned groups of primary photoprotective substances, it is also possible to use secondary photoprotective agents of the antioxidant type which interrupt the photochemical reaction chain which is triggered when UV radiation penetrates into the skin.

Biogenic active ingredients are to be understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prune extract, bambara nut extract and vitamin complexes.

Deodorizing active ingredients counteract, mask or eliminate body odors. Body odors are formed through the action of skin bacteria on apocrine perspiration, during which unpleasant-smelling degradation products are formed. Accordingly, suitable deodorizing active ingredients are, inter alia, antibacterial agents, enzyme inhibitors, odor absorbers or odor maskers.

Suitable insect repellants are, for example, N,N-diethyl-m-toluamide, 1,2-pentanediol or ethyl 3-(N-n-butyl-N-acetylamino)propionate), which is sold under the name Insect Repellent® 3535 by Merck KGaA, and also butylacetylaminopropionates.

A suitable self-tanning agent is dihydroxyacetone. Suitable tyrosine inhibitors, which prevent the formation of melanin and are used in depigmentation compositions, are, for example, arbutin, ferulic acid, kojic acid, coumaric acid and ascorbic acid (vitamin C).

Suitable preservatives are, for example, phenoxyethanol, formaldehyde solution, parabens, pentanediols or sorbic acid, and also the silver complexes known under the name Surfacine® and the further substance classes listed in Appendix 6, Part A and B of the Cosmetics Ordinance.

Perfume oils which may be mentioned are mixtures of natural and synthetic fragrances. Natural fragrances are extracts from flowers, stems and leaves, fruits, fruit peels, roots, woods, herbs and grasses, needles and branches, resins and balsams. Also suitable are animal raw materials, such as, for example, civet and castoreum, and also synthetic fragrance compounds of the ester, ether, aldehyde, ketone, alcohol and hydrocarbon types.

Suitable pearlescent waxes, in particular for use in surface-active formulations, are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter simultaneously serving as foam stabilizers.

Stabilizers which can be used are metal salts of fatty acids, such as, for example, magnesium, aluminum and/or zinc stearate and/or ricinoleate.

To improve the flow behavior, hydrotropes, such as, for example, ethanol, isopropyl alcohol, or polyols, can also be used. Polyols which are suitable here preferably have 2 to 15 carbon atoms and at least two hydroxyl groups. The polyols can also contain further functional groups, in particular amino groups, and/or be modified with nitrogen.

The preparations according to the invention, the compositions according to the invention and the esters according to the invention are suitable in particular in cosmetic and/or pharmaceutical preparations for the wetting or impregnation or coating of utility wipes and hygiene wipes which are used for body cleaning and/or for body care.

Utility wipes and hygiene wipes which may be mentioned by way of example are: tissues, papers, wipes, fleece products, sponges, puffs, plasters and bandages which are used in the area of hygiene and care. These may be wet wipes for baby hygiene and baby care, cleansing wipes, face cleansing wipes, skincare wipes, care wipes with active ingredients to combat skin aging, wipes with sunscreen formulations and insect repellants, and also wipes for decorative cosmetics or for aftersun treatment, toilet wet wipes, antiperspirant wipes, diapers, tissues, wet wipes, hygiene products and self-tanning wipes.

EXAMPLES

Example 1

Preparation of 2-Ethylbutyl Caproate 580.8 g (5 mol) of caproic acid, 613.1 g (6 mol) of 2-ethylbutanol and 0.34 g of tin oxalate ("Fascat 2001") were heated to 160° C. under $N_2$, during which water separation was observed. Once water separation had subsided, the mixture was heated to 210° C. in 10° C. steps. This temperature was then held for 3 h. Then, firstly the excess alcohol was removed by distillation and then the product was distilled at 13-31 mbar and 114-124° C. The product (879.9 g) was obtained as a clear liquid with an acid number of 0.26 and an OH number of 2.17.

Example 2

Preparation of 2-Ethylbutyl Caprylate 187.2 g (1.3 mol) of caprylic acid, 214.0 g (2.09 mol) of 2-ethylbutanol and 0.14 g of tin oxalate ("Fascat 2001") were heated to 160° C. under $N_2$, during which water separation was observed. Once water separation had subsided, the mixture was heated to 210° C. in 10° C. steps. This temperature was then held for 3 h. Then, firstly the excess alcohol was removed by distillation and then the product was distilled at 8-12 mbar and 136-141° C. The product (225.6 g) was obtained as a clear liquid with an acid number of 0.47 and an OH number of 1.36.

Formulations

TABLE 1

Oil-in-water emulsions

| Ingredients: trade name (INCI) | 1 | 2 | 3 | 4 | 5 |
|---|---|---|---|---|---|
| Emulgade ® PL 68/50 (Cetearyl Glucoside, Cetearyl Alcohol) | 4.50 | 4.50 | 4.50 | | |
| Eumulgin ® VL75 (Lauryl Glucoside, Polyglyceryl-2 Dipolyhydroxystearate, Glycerol) | | | | 4.50 | 4.50 |
| 2-Ethylbutyl caprylate | 14.00 | 16.00 | | | 16.00 |
| 2-Ethylbutyl caproate | | | 16.00 | 12.00 | |
| Carbopol ® 980 | | | | 0.30 | 0.30 |
| Lanette ® O | | | | | |
| KOH (20% strength) | | | | 0.70 | 0.70 |
| Glycerol 99.5% strength | 3.00 | 3.00 | 3.00 | 3.00 | 3.00 |
| Formalin solution 37% strength | 0.15 | 0.15 | 0.15 | 0.15 | 0.15 |
| Water dist. | ad 100 | ad 100 | ad 100 | ad 100 | ad 100 |

TABLE 2

Oil-in-water emulsions

| Ingredients: trade name (INCI) | 6 | 7 | 8 | 9 |
|---|---|---|---|---|
| Eumulgin ® VL75 (Lauryl Glucoside, Polyglyceryl-2 Dipolyhydroxystearate, Glycerol) | 4.50 | | | |
| Eumulgin ® B2 (Ceteareth-20) | | 2.00 | 2.00 | 2.00 |
| 2-Ethylbutyl caprylate | | 14.00 | 16.00 | |
| 2-Ethylbutyl caproate | 16.00 | | | 16.00 |
| Carbopol ® 980 | 0.30 | | | |
| Lanette ® O | | 5.00 | 5.00 | 5.00 |
| KOH (20% strength) | 0.70 | | | |
| Glycerol 99.5% strength | 3.00 | 3.00 | 3.00 | 3.00 |
| Formalin solution 37% strength | 0.15 | 0.15 | 0.15 | 0.15 |
| Water dist. | ad 100 | ad 100 | ad 100 | ad 100 |
| pH value | 6.70 | 7.10 | 5.70 | 6.80 |

TABLE 3

Water-in-oil emulsions

| Ingredients: trade name (INCI) | 10 | 11 | 12 | 13 | 14 | 15 |
|---|---|---|---|---|---|---|
| Dehymuls ® LE (PEG-30-Dipolyhydroxystearate) | 5.00 | 5.00 | 5.00 | | | |
| Dehymuls ® PGPH (Polyglyceryl-2-Dipolyhydroxystearate) | | | | 4.00 | 4.00 | 4.00 |
| Lameform ® TGI (Polyglyceryl-3-Diisostearate) | | | | 2.00 | 2.00 | 2.00 |
| 2-Ethylbutyl caprylate | 20.00 | | 18.00 | 20.00 | | 18.00 |
| 2-Ethylbutyl caproate | | 20.00 | | | 20.00 | |
| MgSO4*7H2O | 1.00 | 1.00 | 1.00 | 1.00 | 1.00 | 1.00 |
| Glycerol 99.5% strength | 5.00 | 5.00 | 5.00 | 5.00 | 5.00 | 5.00 |
| Formalin solution 37% strength | 0.15 | 0.15 | 0.15 | 0.15 | 0.15 | 0.15 |
| Water dist. | ad 100 | ad 100 | ad 100 | ad 100 | ad 100 | ad 100 |

TABLE 4

Water-in-oil emulsions

| Ingredients: trade name (INCI) | 16 | 17 | 18 |
|---|---|---|---|
| Dehymuls ® LE (PEG-30-Dipolyhydroxystearate) | 4.00 | 4.00 | 4.00 |
| Lameform ® TGI (Polyglyceryl-3-Diisostearate) | 2.00 | 2.00 | 2.00 |
| 2-Ethylbutyl caprylate | 20.00 | | |
| 2-Ethylbutyl caproate | | 20.00 | 15.00 |
| MgSO4*7H2O | 1.00 | 1.00 | 1.00 |
| Glycerol 99.5% strength | 5.00 | 5.00 | 5.00 |
| Formalin solution 37% strength | 0.15 | 0.15 | 0.15 |
| Water dist. | ad 100 | ad 100 | ad 100 |

Further Formulation Examples

| Example 19: Hair Conditioner | | Example 20: Nanoemulsion | |
|---|---|---|---|
| Dehyquart ® A CA (Cetrimonium Chloride) | 4.5% | Monomuls ® 90 O 18 (Glyceryl Oleate) | 6.11% |
| Lanette ® O (Cetearyl Alcohol) | 4% | 2-Ethylbutyl caprylate | 17.88% |
| Cutina ® CP (Cetyl Palmitate) | 1% | Eutanol ® G (Octyldodecanol) | 5.97% |
| 2-Ethylbutyl caprylate | 1.5% | Plantapon ® LGC Sorb (Sodium Lauryl Glucose Carboxylate (and) Lauryl Glucoside) | 9.5% |
| Eumulgin ® B2 (Ceteareth-20) | 0.3% | | |
| Preservative | q.s. | Plantapon ® ACG 35 (Disodium Cocoyl Glutamate) | 0.78% |
| Aqua demin. | ad 100 | | |
| | | Phenoxyethanol | 0.5% |
| | | Phenonip | 0.5% |
| | | Aqua. demin. | ad 100 |

TABLE 5

| Trade name (INCI) | 21 | 22 | 23 | 24 | 25 | 26 | 27 |
|---|---|---|---|---|---|---|---|
| Emulgade ® SE-PF (Glyceryl Stearate, Ceteareth-20, Ceteareth-12, Cetearyl Alcohol, Cetyl Palmitate) | 4.80 | | | | | | |
| Euraulgin ® B2 (Ceteareth-20) | 3.70 | | 3.00 | | | | |
| Emulgade ® PL-68/50 (Cetearyl Glucose, Cetearyl Alcohol) | | | | 5.00 | | | |
| Eumulgin ® SG (Sodium Stearoyl Glutamate) | | | | 0.50 | 0.20 | | |
| Eumulgin ® VL 75 (Lauryl Glucoside, Polyglyceryl-2 Dipolyhydroxystearate, Glycerin) | | 6.00 | | | | | 0.50 |
| Cutina ® MD (Glyceryl Stearate) | | | | 2.00 | | | |
| Cutina ® PES (Pentaerythrityl Distearate) | | | | | 1.00 | | |
| 2-Ethylbutyl caprylate | 5.00 | 7.00 | 2.00 | 5.00 | 5.00 | 5.00 | 6.00 |
| Cetiol ® 868 (Ethylhexyl Stearate) | | | 7.00 | 4.00 | | | |
| Cetiol ® AB (C12-15 Alkyl Benzoate) | | 7.00 | | | | | |
| Cetiol ® LC (Coco-Caprylate/Caprate) | | | | | 5.00 | 5.00 | |
| Myritol ® 331 (Cocoglycerides) | 3.00 | | | | | | 10.00 |
| Myritol ® 312 (Caprylic/Capric Triglyceride) | | | | 5.00 | | | |
| Myritol ® 318 (Caprylic/Capric Triglyceride) | | | 7.00 | | | | |
| Dimethicone (Wacker AK 350) | | | | 0.50 | | | |
| Ethylhexyl Methoxycinnamate (Uvinul MC 80) | 5.00 | 7.50 | | | | | 7.50 |
| 4-Methylbenzylidene Camphor (Neo Helipan MBC) | 2.00 | | | | | | |
| Butyl Methoxydibenzoylmethane (Parsol 1789) | 1.50 | 3.50 | | | | | 2.00 |
| Copherol ® F 1300 C (Tocopherol) | | | | 1.00 | | | 1.00 |
| Cosmedia ® DC (Hydrogenated Dimer Dilinoleyl/Dimethylcarbonate Copolymer) | | | | | | | 2.00 |
| Cosmedia ® SP (Sodium Polyacrylate) | | 0.50 | 0.20 | | 1.00 | 1.00 | 0.30 |
| Glycerol | 5.00 | | | 2.00 | 5.00 | | 5.00 |
| 1,3-Butylene Glycol | | 3.00 | | 2.00 | | | |
| Phenylbenzimidazole Sulfonic Acid (Neo Heliopan Hydro, 15% aqueous solution) | 13.30 | | | | | | |
| Methylene Bis-Benzotriazolyl Tetramethylbutylphenol (Tinosorb M) | | 5.00 | | | | | |
| Tapoica starch | | | | | | | |
| Water, preservative q.s. | | | | | | | |
| NaOH (10%) | pH 7.0 | pH 6.6 | pH 6.3 | pH 7.0 | pH 6.1 | pH 6.5 | pH 6.0 |

TABLE 6

| Trade name (INCI) | 28 | 29 | 30 | 31 |
|---|---|---|---|---|
| Dehymuls ® PGPH (Polyglyceryl-2 Dipolyhydroxystearate) | 2.00 | 2.00 | | |
| Dehymuls ® LE (PEG-30 Dipolyhydroxystearate) | | | 2.00 | |
| Cyclopentasiloxane, Caprylyl Dimethicone, Ethoxy Glucoside (Wacker Belsil SPG 128 VP) | 12.00 | | | |
| Beeswax 8100 (Kahl) | 1.00 | | | |
| Zinc stearate (Zinkum 29) | 1.00 | | | |
| Texapon ® NSO (Sodium Laureth Sulfate) | | | | 34.00 |
| Dehyton ® PK 45 (Cocamidopropyl Betaine) | | | | 8.00 |
| Emulgade ® NLB (Steareth-2, Ceteareth-12, Stearyl Alcohol, Ceteareth-20, Distearyl Ether) | | | | 3.00 |
| Polyquaterium-10 (Polymer JR 400) | | | | 0.20 |
| Acrylates Copolymer (Carbopol Aqua SF-1) | | | | 8.00 |
| 2-Ethylbutyl caproate | 8.00 | 6.00 | 10.00 | 3.00 |
| Cetiol ® 868 (Ethylhexyl Stearate) | 7.00 | | | |
| Cetiol ® A (Hexyl Laurate) | | 6.00 | | |
| Cetiol ® SN (Cetearyl Isononanoate) | | 7.00 | | |
| Eutanol ® G 16 (Hexyldecanol) | | 3.00 | | |
| Myritol ® 331 (Cocoglycerides) | | | 31.00 | |
| Helianthus Annuus (sunflower oil) | | | 57.00 | |
| Copherol ® 1250 C (Tocopheryl Acetate) | | | 1.00 | |
| Copherol ® F 1300 C (Tocopherol) | 1.00 | | | |
| Glycerol | | 5.00 | | |
| 1,3-Butylene Glycol | 3.00 | | | |
| Sodium Chloride | 0.40 | | | |
| Magnesium Sulfate Heptahydrate | | | 1.00 | |

TABLE 6-continued

| Trade name (INCI) | 28 | 29 | 30 | 31 |
|---|---|---|---|---|
| Alcohol (Ethanol) | | 4.00 | | |
| Hydagen ® (Bisabolol) | | | 0.50 | |
| Water, preservative q.s. | ad 100 | ad 100 | | ad 100 |

TABLE 7

| Trade name (INCI) | 32 | 33 | 34 |
|---|---|---|---|
| Emulgade ® NLB (Steareth-2, Ceteareth-12, Stearyl Alcohol, Ceteareth-20, Distearyl Ether) | 5.00 | 5.00 | |
| Lanette ® 18 (Stearyl Alcohol) | | | 14.70 |
| Cutina ® HR (Hydrogenated Castor Oil) | | | 3.70 |
| 2-Ethylbutyl caproate | 6.00 | 4.50 | 23.70 |
| Cyclomethicone (Dow Corning 245) | | 1.50 | 35.00 |
| Aluminium Chlorhydrate (Chlorhydrol 50% strength) | 40.00 | 20.00 | |
| Aluminium Zirconium Tetrachlorohydrex GLY (Rezal 36 GP) | | | 22.90 |
| Water | ad 100 | ad 100 | |

Footnotes to tables:
RT = room temperature 20° C.; rpm = revolutions per minute

The invention claimed is:

1. A method of preparing cosmetic preparations, the method comprising incorporating 2-ethylbutanol esters of C6-C26-carboxylic acids or 2-ethylbutanol esters of C6-C26-dicarboxylic acids as an odorless oil component of an o/w emulsion in a cosmetic preparation, provided that 2-ethylbutyl 2-methylpentanoate is excluded, wherein said carboxylic acids or dicarboxylic acids are linear and unbranched.

2. A method of preparing pharmaceutical preparations, the method comprising incorporating 2-ethylbutanol esters of C6-C26-carboxylic acids or 2-ethylbutanol esters of C6-C26-dicarboxylic acids as an odorless oil component of an o/w emulsion in pharmaceutical preparation, provided that 2-ethylbutyl 2-methylpentanoate is excluded, wherein said carboxylic acids or dicarboxylic acids are linear and unbranched.

3. A method of preparing cosmetic and/or pharmaceutical preparations, the method comprising incorporating 2-ethylbutanol esters of C6-C26-carboxylic acids or 2-ethylbutanol esters of C6-C26-dicarboxylic acids in a cosmetic and/or pharmaceutical preparation, wherein said esters are incorporated as odorless oil bodies in an o/w emulsion, wherein said carboxylic acids or dicarboxylic acids are linear and unbranched.

4. The method of claim 1, further comprising incorporating one or more components selected from the group consisting of an emulsifier, a surfactant, a wax, a polymer, and an oil body into the cosmetic preparations.

5. The method of claim 2, further comprising incorporating one or more components selected from the group consisting of an emulsifier, a surfactant, a wax, a polymer, and an oil body into the pharmaceutical preparation.

6. The method of claim 3, wherein the esters comprise an ester of 2-ethylbutanol with C9-C16-carboxylic acids.

7. The method of claim 6, wherein the esters are selected from the group consisting of 2-ethylbutyl n-nonanoate, 2-ethylbutyl isononanoate, 2-ethylbutyl n-decanoate, 2-ethylbutyl isodecanoate, 2-ethylbutyl n-undecanoate, 2-ethylbutyl isoundecanoate, 2-ethylbutyl n-undecenoate, 2-ethylbutyl n-dodecanoate, 2-ethylbutyl isododecanoate, 2-ethylbutyl n-tridecanoate, 2-ethylbutyl isotridecanoate, 2-ethylbutyl n-tetradecanoate, 2-ethylbutyl isotetradecanoate, 2-ethylbutyl n-pentadecanoate, 2-ethylbutyl isopentadecanoate, 2-ethylbutyl n-hexadecanoate, 2-ethylbutyl isohexadecanoate, and 2-ethylbutyl benzoate.

8. The method of claim 3, wherein the esters comprise an ester of 2-ethylbutanol with C8-, C11-, C12-, or C14C26-dicarboxylic acids or unsaturated C6-, C7-, C9-, C10-, or C13-dicarboxylic acids.

9. The method of claim 3, wherein the cosmetic and/or pharmaceutical preparations comprises (a) 0.1 - 80% by weight of at least one ester of 2-ethylbutanol with C6-C26-carboxylic acids or C6-C26-dicarboxylic acids, (b) 0.1 - 20% by weight of an emulsifier, a surfactant, a wax component, a polymer, or combinations thereof, (c) 0.1 - 40% by weight of a further oil body, and (d) 0.5 - 98% by weight of water.

* * * * *